United States Patent [19]

Bright

[11] 4,098,993
[45] Jul. 4, 1978

[54] SEMI-SYNTHETIC 4-UREIDO-OLEANDOMYCIN DERIVATIVES

[75] Inventor: Gene M. Bright, Groton, Conn.

[73] Assignee: Pfizer Inc., New York, N.Y.

[21] Appl. No.: 818,907

[22] Filed: Jul. 25, 1977

[51] Int. Cl.² .................. C07H 17/08; A01N 9/00
[52] U.S. Cl. ........................... 536/9; 424/180; 536/17
[58] Field of Search ............................. 536/9

[56] References Cited

U.S. PATENT DOCUMENTS

| 4,036,853 | 8/1977 | Sciavolino | 536/9 |
| 4,069,379 | 1/1978 | Sciavolino | 536/9 |

Primary Examiner—Johnnie R. Brown
Assistant Examiner—Blondel Hazel
Attorney, Agent, or Firm—Francis X. Murphy; Charles J. Knuth; Albert E. Frost

[57] ABSTRACT

A series of 11-alkanoyl-4''-deoxy-4''-ureido-oleandomycin antibacterial agents, their preparation from 11-alkanoyl-4''-deoxy-4''-amino-oleandomycin and their conversion into other 4''-amino derived antibacterial compounds.

15 Claims, No Drawings

SEMI-SYNTHETIC 4-UREIDO-OLEANDOMYCIN DERIVATIVES

BACKGROUND OF THE INVENTION

1. Field of the Invention

This invention relates to novel antibacterial agents and, in particular, to a series of 11-alkanoyl-4"-deoxy-4"-ureido-oleandomycins and their pharmaceutically acceptable acid addition salts. The invention also relates to key intermediates leading to the 4"-ureido compounds and to other 4"-amino derived antibacterial agents.

2. Description of the Prior Art

Oleandomycin, its production in fermentation broths and its use as an antibacterial agent were first described in U.S. Pat. No. 2,757,123. The naturally occurring compound is known to have the following structure:

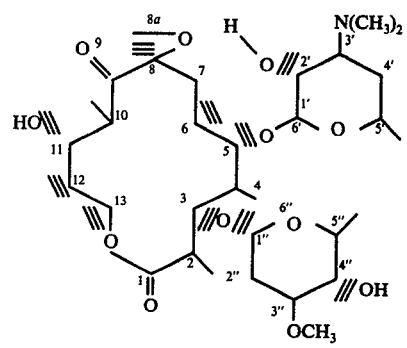

The conventionally accepted numbering scheme and stereochemical representation for oleandomycin and similar compounds is shown at a variety of positions.

Several synthetic modifications of this compound are known, particularly those in which from one to three of the free hydroxyl groups found at the 2', 4" and 11-positions are esterified as acetyl esters. In addition, there are described in U.S. Pat. No. 3,022,219 similar modifications in which the acetyl in the above-mentioned esters is replaced with another, preferably unbranched lower alkanoyl of three to six carbon atoms.

SUMMARY OF THE INVENTION

The semi-synthetic oleandomycin compounds of this invention are of the formulae:

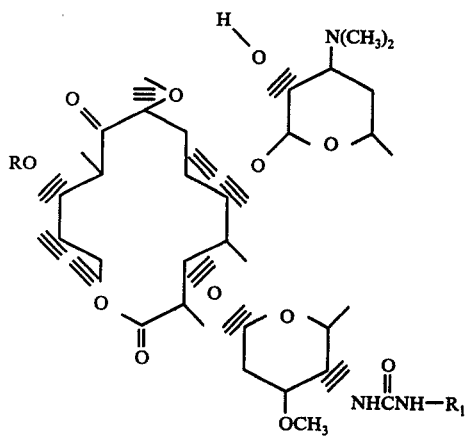

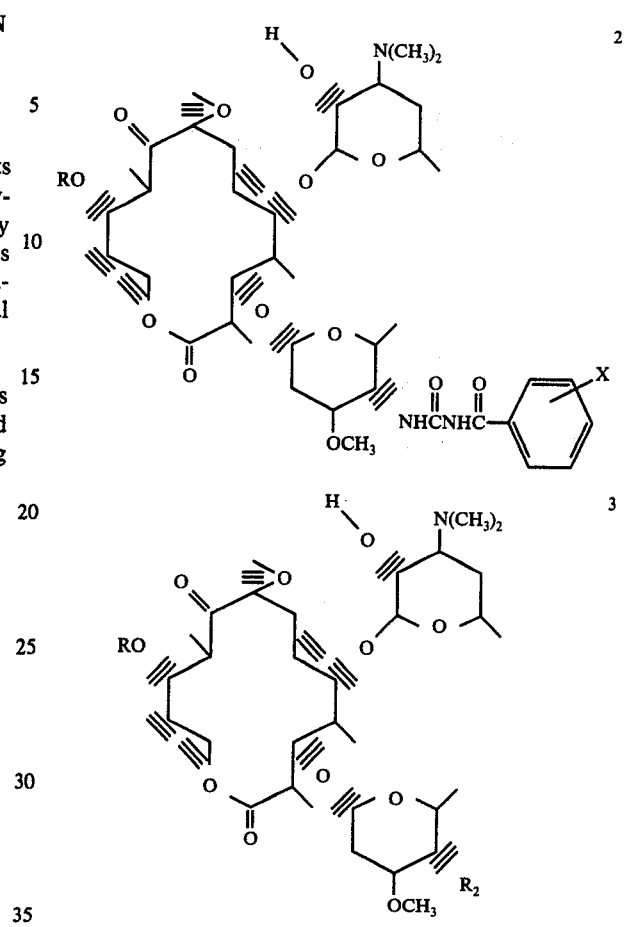

wherein R is alkanoyl having from two to three carbon atoms; $R_1$ is hydrogen, pyridylmethyl, furylmethyl, thenyl, hydroxypyridyl, phenyl, benzyl or substituted phenyl or benzyl wherein said substituent is methyl, chloro, fluoro, methoxy, amino or trifluoromethyl; X is methyl, methoxy, fluoro, chloro or trifluoromethyl; $R_2$ is —N=C=O or —NHCN; and the pharmaceutically acceptable acid addition salts of 1 and 2, and 3 wherein $R_2$ is —NHCN.

Preferred antibacterials related to the compounds of formula 1 are those wherein R is acetyl. Especially preferred species within this group are N-(11-acetyl-4"-deoxy-4"-oleandomycyl)-N'-(p-methoxybenzyl)urea, N-(11-acetyl-4"-deoxy-4"-oleandomycyl)-N'-(p-chlorobenzyl)urea; N-(11-acetyl-4"-deoxy-4"-oleandomycyl)-N'-(o-chlorobenzyl)urea, N-(11-acetyl-4"-deoxy-4"-oleandomycyl)-N'-(m-methylbenzyl)urea, N-(11-acetyl-4"-deoxy-4"-oleandomycyl)-N'-(m-tolyl)urea and N-(11-acetyl-4"-deoxy-4"-oleandomycyl)-N'-(o-methylbenzyl)urea.

Preferred antibacterials related to the compounds of formula 2 are those wherein R is acetyl. Especially preferred species within this group are N-(11-acetyl-4"-deoxy-4"-oleandomycyl)-N'-(m-methylbenzoyl)urea and N-(11-acetyl-4"-deoxy-4"-oleanodomycyl)-N'-(p-methoxybenzoyl)urea.

Preferred within the compounds of formula 3 are those wherein R is acetyl. Especially preferred as an intermediate is 11-acetyl-4"-deoxy-4"-isocyanato-oleandomycin.

DETAILED DESCRIPTION OF THE INVENTION

In accordance with the process for synthesizing the 11-alkanoyl-4''-deoxy-4''-ureido-oleandomycin antibacterials related to 1 the following scheme is illustrative:

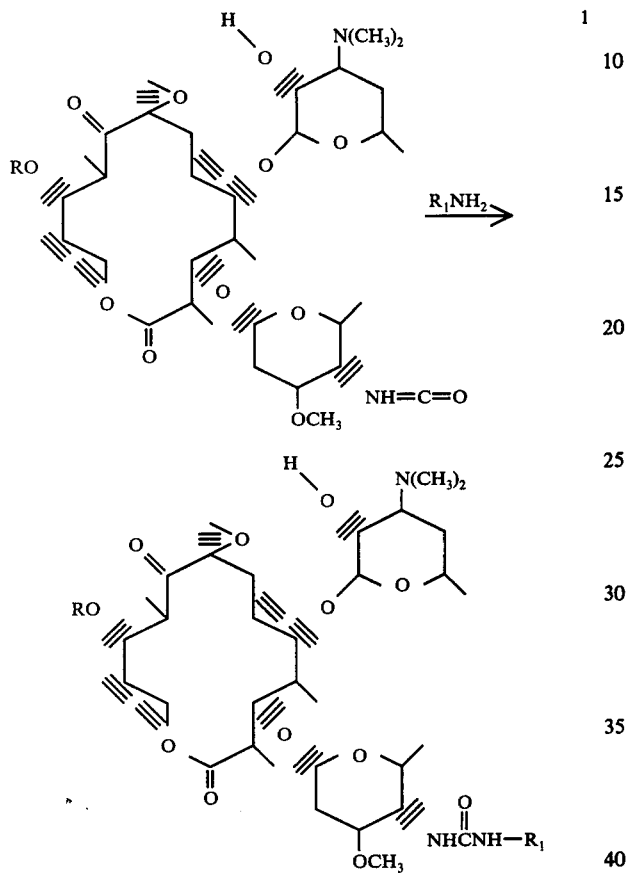

wherein R and $R_1$ are as previously defined.

The appropriate 11-alkanoyl-4''-deoxy-4''-isocyanato-oleandomycin is contacted with the requisite amine in a reaction-inert solvent. Such solvents should appreciably solubilize the reactants while not reacting to any significant extent with either the starting reagents or the products formed. Preferred are aprotic, polar solvents which are immiscible with water. Especially preferred are methylene chloride and chloroform.

In practice, one mole of the isocyanate is contacted with up to four moles of the requisite amine. Alternately, one to two moles of the amine can be employed in conjunction with the balance of the four moles being a tertiary amine, such as triethylamine or pyridine.

Reaction time is not critical and is dependent on reaction temperature, concentration and inherent reactivity of the starting reagents. When the reactions are conducted at ice-bath temperatures at the hereinafter mentioned concentrations, the reaction is essentially complete in 30–60 minutes. The preferred reaction temperature is ice-bath temperature.

The reaction, on completion, is worked-up by the addition of additional solvent and water. The water layer is made strongly basic with an aqueous sodium hydroxide solution and the water immiscible organic phase separated, dried and evaporated to dryness. The crude product can, if desired, be further purified by chromatographing on silica gel, a procedure well known in the art.

An alternate method for synthesizing compounds related to 1 comprises the reaction of the appropriate 11-alkanoyl-4''-deoxy-4''-amino-oleandomycin with the requisite isocyanate as illustrated:

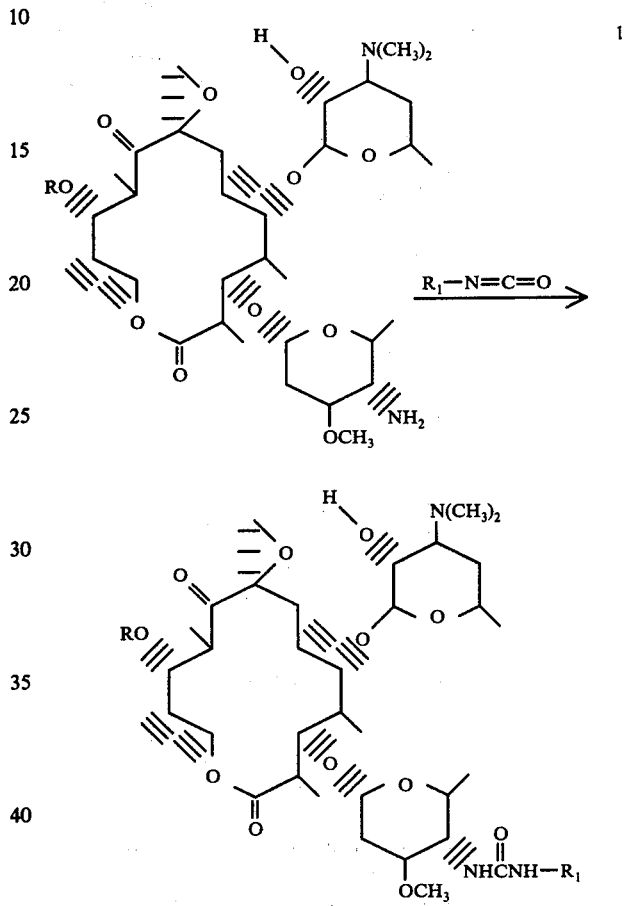

This alternative method for preparing compounds related to 1 is conducted in a similar manner to the initial route. The reactants are contacted in the same type of reaction-inert solvents at ice-bath temperature. It is convenient, in employing this alternate method, to allow the reaction temperature to warm to room temperature aftr the reactants have initially been brought into contact with one another. The reaction at ambient temperatures is complete in 30–60 minutes.

The ratio of 4''-amino-oleandomycin to isocyanate is about one to one with as much as a 10–20% excess of the isocyanate.

At the completion of the reaction the product is worked-up in the same manner as previously discussed.

The antibacterial agents of formula 2 are prepared through the reaction of the appropriate 11-alkanoyl-4''-deoxy-4''-amino-oleandomycin and a benzoyl isocyanate s illustrated:

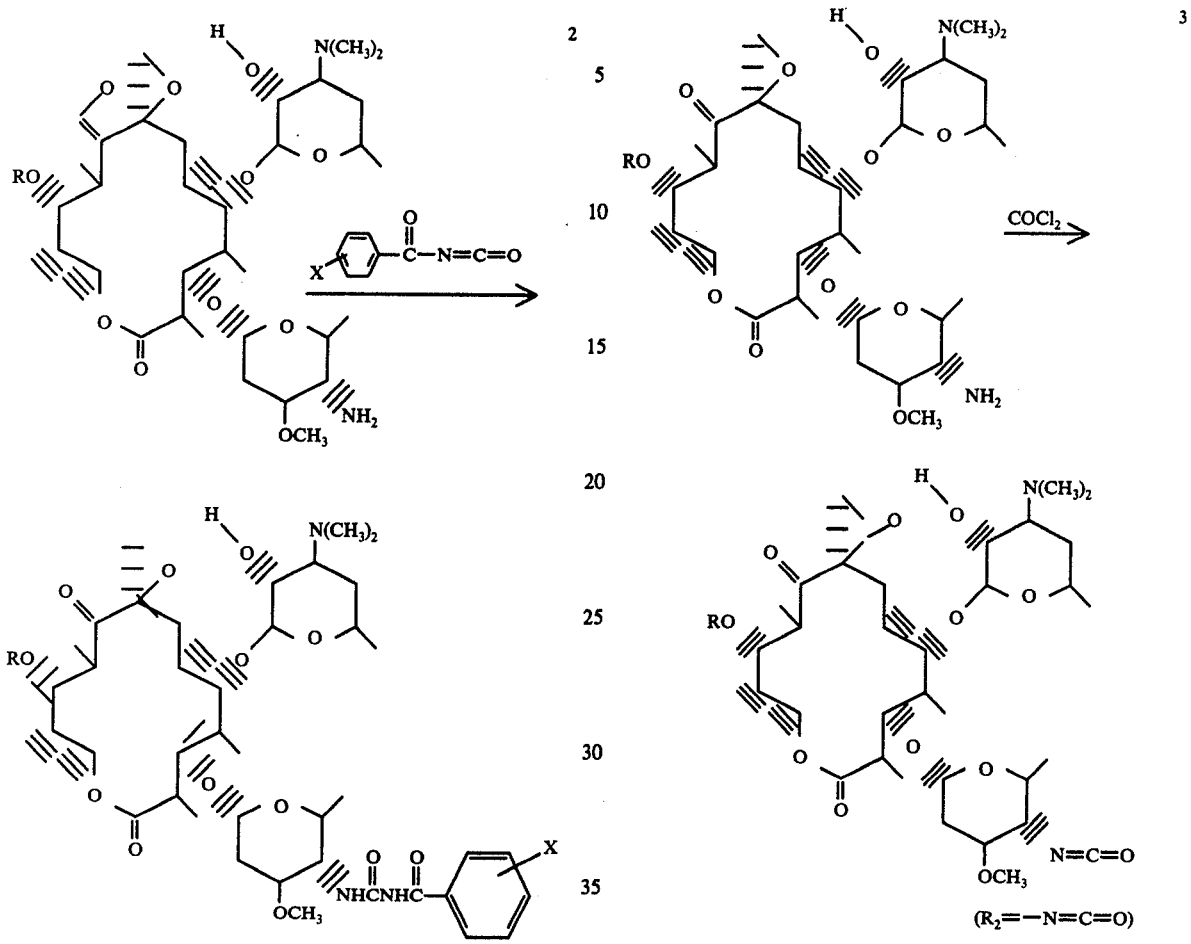

wherein R and X are as previously defined.

The reaction is conducted in a reaction-inert solvent similar to that employed in the routes leading to compounds of formula 1.

In practice one mole of the 11-alkanoyl-4"-deoxy-4"-amino-oleandomycin is contacted with one mole plus as much as a 10-20% excess of the requisite benzoyl isocyanate. The ambient reaction temperature of 25° C. allows for the completion of the reaction in 30-60 minutes.

Again, the reaction is worked-up and the product isolated and purified by the same procedures employed in the processes leading to compounds related to 1.

Those compounds of formula 3 wherein R is as previously defined and $R_2$ is —N=C=O are useful intermediates leading to the compounds of formula 1 through their reactions with amines as hereinbefore discussed, and are prepared by the following illustrative scheme:

In practice, one mole of the 4"-amino compound is contacted with one mole of phosgene plus as much as a 10-20% excess in the presence of three to four moles of a hydrogen chloride scavenger such as pyridine or triethylamine. The reaction is best carried out under anhydrous conditions in a chlorinated hydrocarbon solvent such as methylene chloride or chloroform.

It is preferred to add the phosgene in one of the aforementioned solvents to a cold (0° C.) solution of the 4"-amino compound and hydrogen chloride scavenger dissolved in a similar solvent rapidly with stirring. At the indicated reaction temperature the product is essentially completely formed in 10-20 minutes.

The product is isolated by removal of the solvent and excess acid scavenger, followed by redissolution in fresh solvent, washing with water to remove scavenger amine hydrochloride and removing the solvent in vacuo. No further purification of the intermediate is necessary.

Synthesis of the antibacterial compounds of formula 3 wherein R is as previously indicated and $R_2$ is —NHCN is carried out through the dehydration of the corresponding 4"-ureido compound of formula 1 ($R_1$=H) as follows:

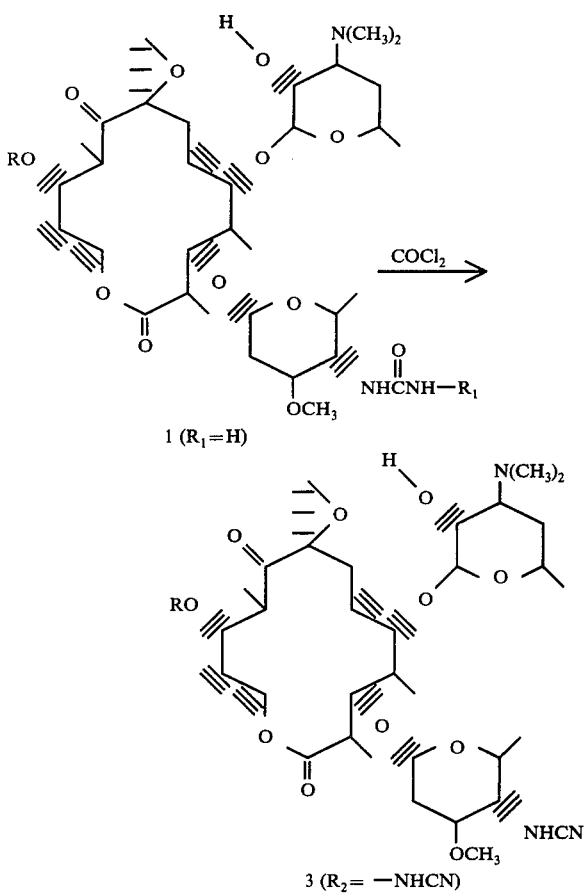

1 (R₁=H)

3 (R₂= —NHCN)

Experimentally, one mole of the 4"-ureido compound and four to five moles of a hydrogen chloride scavenger in one of the aforementioned chlorinated hydrocarbon solvent at 0° C. is treated with ten moles of phosgene in a similar solvent.

When the preferred reaction temperature of 0° C. is employed, the reaction is substantially complete in 10-20 minutes.

The product can be isolated in the same manner as previously described for compounds of formula 3 wherein R₂ is —N═C═O.

The starting 4"-amino compounds used in the synthesis of antibacterial agents of the present invention are synthesized by oxidation of the natural oleandomycin followed by a reductive amination of the resultant ketone as hereinafter described. The isocyanates employed in the processes for preparing compounds of formulae 1 and 2 are either commercially available or are synthesized according to the procedures as taught by Speziale et al., *J. Org. Chem.*, 30, 4306 (1965) and Wagner and Zook, "Synthetic Organic Chemistry", John Wiley and Sons, New York, N.Y., 1956, p. 640.

In the utilization of the chemotherapeutic activity of those compounds of the present invention which form salts, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic, gluconic and aspartic acids.

The novel 4"-deoxy-4"-amino-oleandomycin derivatives described herein exhibit in vitro activity against a variety of Gram-positive microorganisms such as *Staphylococcus aureus* and *Streptococcus pyogenes* and against certain Gram-negative microorganisms such as those of spherical or ellipsoidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g., sick-room utensils; and as industrial antimicrobials, for example, in water treatment, slime control, paint and wood preservation.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvent, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive microorganisms via the oral and/or parenteral routes of administration in animals, including man. Their in vivo activity is more limited as regards susceptible organisms and is determined by the usual procedure which comprises mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for four days after the last treatment and the number of survivors is noted.

When used in vivo, these novel compounds can be administered orally or parenterally, e.g., by subcutaneous or intramuscular injection, at a degree of from about 5 mg./kg. to about 200 mg./kg. of body weight per day. The favored dosage range is from about 25 mg./kg. to about 100 mg./kg. of body weight per day and the preferred range from about 50 mg./kg. to about 75 mg./kg. of body weight per day. Vehicles suitable for parenteral injection may be either aqueous such as water, isotonic saline, isotonic dextrose, Ringers' solution, or non-aqueous such as fatty oils or vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

The following examples are provided solely for the purpose of illustration and are not to be construed as limitations of this invention, many variations of which are possible without departing from the spirit or scope thereof.

EXAMPLE 1

11-Acetyl-4''-deoxy-4''-isocyanato-oleandomycin

To a solution of 5.0 g. (6.6 mmoles) of 11-acetyl-4''-deoxy-4''-amino-oleandomycin and 1.65 ml. (20.5 mmoles) of pyridine in 100 ml. of anhydrous methylene chloride cooled to 0° C. is added 18.3 ml. of a 0.41M solution of phosgene in chloroform with rapid stirring. After 10 min. stirring at 0° C. the solvent and excess pyridine are removed in vacuo leaving the crude product as a yellow foam. The residue is dissolved in 100 ml. of methylene chloride which is washed (2 × 100 ml.) with water and dried over sodium sulfate. The solvent is removed under reduced pressure to provide the desired 4.0 g. of the product.

NMR ($\delta$, CDCl$_3$): 2.09 (3H)s; 2.61 (6H)s; 2.68 (2H)m; and 3.45 (3H)s.

In a similar manner, starting with 11-propionyl-4''-deoxy-4''-amino-oleandomycin, 11-propionyl-4''-deoxy-4''-isocyanato-oleandomycin is prepared.

EXAMPLE 2

11-Acetyl-4''-deoxy-4''-ureido-oleandomycin

To 3.02 g (4.0 mmoles) of 11-acetyl-4''-deoxy-4''-isocyanato in 70 ml. of tetrahydrofuran at ambient temperatures is added 0.928 ml. of concentrated aqueous ammonium hydroxide (12 mmoles) over a 10 min. period. The yellow foam, which remains after the reaction mixture is evaporated to dryness, is chromatographed on a 3.25 × 38 cm. silica gel-acetone packed column. The initial eluting solvent is acetone. Methanol is gradually added to the eluting solvent until the final elution when it is 25% by volume.

The column fractions, shown by thin layer chromatography to be pure, are combined and the solvent removed in vacuo to give 2.30 g. of the desired product as an amorphous solid.

NMR ($\delta$, CDCl$_3$): 2.10 (3H)s; 2.36 (6H)s; 2.70 (2H)m; 3.47 (3H)s; and 5.70 (1H)b.

EXAMPLE 3

11-Acetyl-4''-deoxy-4''-cyanamido-oleandomycin

To 570 mg. (0.74 mmoles) of 11-acetyl-4''-deoxy-4''-ureido-oleandomycin and 0.5 ml. (3.6 mmoles) of triethylamine in 25 ml. of anhydrous methylene chloride cooled to 0° C. is added 1.80 ml. of a 0.41M solution of phosgene in chloroform (7.4 mmoles). After 5 min. of stirring in the cold, the reaction is diluted with 100 ml. of methylene chloride. The resulting solution is washed with water (3 × 100 ml.), dried over sodium sulfate and concentrated under reduced pressure to afford 400 mg. of the desired product as an amorphous solid.

NMR ($\delta$, CDCl$_3$): 2.10 (3H)s; 2.30 (6H)s; 2.64 (2H)m; and 3.44 (3H)s.

EXAMPLE 4

N-(11-Acetyl-4''-deoxy-4''-oleandomycyl)-N'-benzylurea

A cold (0° C.) solution of 3.0 g. (4.11 mmoles) of 11-acetyl-4''-deoxy-4''-amino-oleandomycin and .99 ml. of pyridine in 60 ml. of dry methylene chloride is rapidly stirred while 10.98 ml. of a .41M solution of phosgene in chloroform is added rapidly. After 5 min. 1.8 ml. of benzylamine is added and the stirring continued in the cold for an additional 15 min. The reaction is diluted with 150 ml. of methylene chloride, layered with 150 ml. of water and pH of the aqueous layer adjusted to 9.5 with aqueous 6N sodium hydroxide solution. The separated organic layer is washed with water (3 × 150 ml.), dried over sodium sulfate and concentrated to an amber foam in vacuo. The residue is chromatographed on a 3.5 × 37 cm. silica gel-acetone packed column using acetone as the eluate. Fractions 100–119, comprising 5 ml. each, are combined and concentrated to dryness to give 69 mg. of the desired product. Similarly, fractions 120–195 are combined and concentrated to dryness to give 451 mg. of the desired product.

NMR ($\delta$, CDCl$_3$): 2.08 (3H)s; 2.34 (6H)s; 2.68 (2H)m; 3.4 (3H)s; and 7.34 (5H)s.

EXAMPLE 5

Starting with the appropriate benzylamine and employing the procedure of Example 4, the following compounds are prepared:

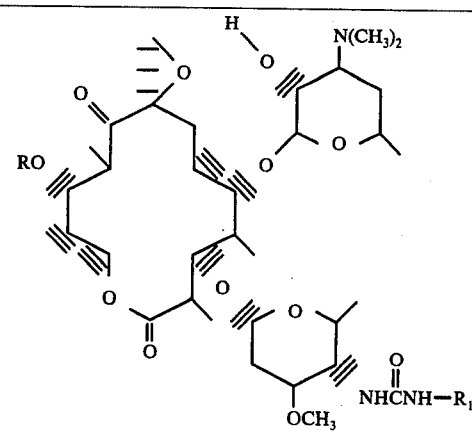

| R | R$_1$ | $\delta$, CDCl$_3$ |
|---|---|---|
| CH$_3$C(O)— | (2-CH$_3$-C$_6$H$_4$)CH$_2$— | 2.08 (3H)s; 2.33 (6H)s; 2.36 (3H)s; 2.65 (2H)m; 3.41 (3H)s; and 7.09–7.34 (4H)m. |

-continued

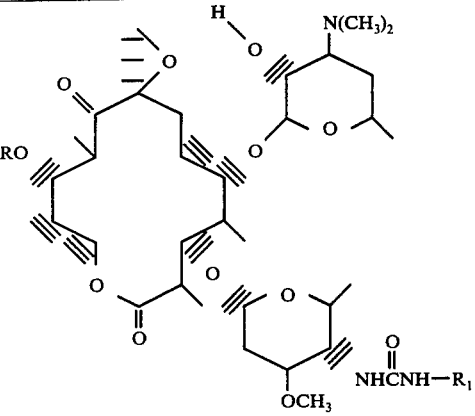

| R | R₁ | δ, CDCl₃ |
|---|----|----------|
| CH₃C(O)— | CH₃ | 2.06 (3H)s; 2.34 (6H)s; 2.37 (3H)s; 2.67 (2H)m; 3.40 (3H)s; and 7.19 (4H)m. |

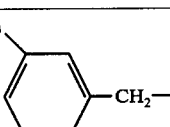

EXAMPLE 6

The procedure of Example 4 is again repeated, starting with the appropriate reagents, to give the following analogs; N-(11-propionyl-4″-deoxy-4″-oleandomycyl)-N′-benzylurea; N-(11-acetyl-4″-deoxy-4″-oleandomycyl)-N′-(p-methylbenzyl)urea; N-(11-propionyl-4″-deoxy-4″-oleandomycyl)-N′-(o-methylbenzyl)-urea; N-(11-propionyl-4″-deoxy-4″-oleandomycyl)-N′-(p-methylbenzyl)urea; and N-(11-propionyl-4″-deoxy-4″-oleandomycyl)-N′-(m-methylbenzyl)urea.

EXAMPLE 7

N-(11-Acetyl-4″-deoxy-4″-oleandomycyl)-N′-(o-chlorobenzyl)urea

A .3M solution of phosgene in chloroform (10 ml.) is added rapidly with stirring to a solution of 2.0 g. (2.7 mmoles) of 11-acetyl-4″-deoxy-4″-amino-oleandomycin and .65 ml. of pyridine in 50 ml. of dry methylene chloride cooled to 0° C. in an ice bath. The solvent is removed under reduced pressure, and the residual yellow foam dissolved in 50 ml. of dry methylene chloride. The solution is cooled with an ice bath and treated with 1.08 ml. of o-chlorobenzylamine.

After 30 min. the reaction solution is washed with water (2 × 100 ml.), the pH being adjusted to 9.5 with 6N aqueous sodium hydroxide solution during the final washing. The methylene chloride layer is separated, dried over sodium sulfate and concentrated in vacuo to give 3.3 g. of the desired product as a yellow foam.

The product is further purified by chromatographing on a 3.25 × 38 cm., silica gel-acetone packed column, using acetone as the eluate. Fractions 201–300, comprising 5 ml. each, are combined and concentrated to dryness to give 1.9 g. of the pure product.

NMR (δ, CDCl₃): 2.7 (3H)s; 2.31 (6H)s; 2.66 (2H)m; 3.41 (3H)s; and 7.1–7.59 (4H)m.

Also prepared by the procedure of Example 7, when the requisite starting materials are employed, are:
N-(11-acetyl-4″-deoxy-4″-oleandomycyl)-N′-(p-chlorobenzyl)urea NMR (δ, CDCl₃): 2.15 (3H)s; 2.31 (6H)s; 2.66 (2H)m; 3.39 (3H)s; and 7.27 (4H)s.
N-(11-acetyl-4″-deoxy-4″-oleandomycyl)-N′-(2,4-dichlorobenzyl)urea NMR (δ, CPCl₃): 2.10 (3H)s; 2.34 (6H)s; 2.70 (2H)m; 3.45 (3H)s; and 7.28–7.60 (3H)m.
N-(11-acetyl-4″-deoxy-4″-oleandomycyl)-N′-(3,4-dichlorobenzyl)urea NMR (δ, CDCl₃): 2.10 (3H)s; 2.35 (6H)s; 2.69 (2H)m; 3.45 (3H)s; and 7.06–7.56 (3H)m.
N-(11-acetyl-4″-deoxy-4″-oleandomycyl)-N′-(o-fluorobenzyl)urea NMR (δ, CDCl₃): 2.07 (3H)s; 2.36 (6H)s; 2.71 (2H)m; 3.45 (3H)s; and 6.89–7.65 (4H)m.

EXAMPLE 8

Employing the procedure of Example 7 and starting with the appropriate reagents, the following congeners are synthesized: N-(11-propionyl-4″-deoxy-4″-oleandomycyl)-N′-(o-chlorobenzyl)urea; N-(11-propionyl-4″-deoxy-4″-oleandomycyl)-N′-(p-chlorobenzyl)urea; N-(11-acetyl-4″-deoxy-4″-oleandomycyl)-N′-(m-chlorobenzyl)urea; N-(11-acetyl-4″-deoxy-4″-oleandomycyl)-N′-(m-fluorobenzyl)urea; N-(11-propionyl-4″-deoxy-4″-oleandomycyl)-N′-(p-fluorobenzyl)urea; N-(11-acetyl-4″-deoxy-4″-oleandomycyl)-N′-(o-trifluoromethylbenzyl)urea; N-(11-propionyl-4″-deoxy-4″-oleandomycyl)-N′-(p-trifluoromethylbenzyl)urea; and N-(11-acetyl-4″-deoxy-4″-oleandomycyl)-N′-(m-trifluoromethylbenzyl)urea.

EXAMPLE 9

N-(11-Acetyl-4″-deoxy-4″-oleandomycyl)-N′-(p-methoxybenzyl)urea

To a solution of 2.0 g. (2.7 mmoles) of 11-acetyl-4″-deoxy-4″-aminooleandomycin and .65 ml. of pyridine in 50 ml. of dry methylene chloride cooled to 0° C. is added rapidly with stirring 10 ml. of a .3M solution of phosgene in chloroform.

The solvent is removed under vacuum and the residue dissolved in 50 ml. of dry methylene chloride. After cooling in an ice bath 1.35 ml. of p-methoxybenzylamine is added and the reaction mixture allowed to stir at ice bath temperatures for one hour. Methylene chloride (100 ml.) is added to the reaction mixture followed by 100 ml. of water. The organic layer is separated and washed with fresh water and the pH adjusted to 9.5 with 6N aqueous sodium hydroxide solution. The organic phase is subsequently separated, dried over sodium sulfate and concentrated to give 2.5 g. of a yellow foam.

The product is further purified by chromatographing on silica gel using acetone as the eluate. Fractions, which are comprised of 5 ml. each, 221–395 are combined and concentrated in vacuo to dryness to give 1.4 g. of the product.

NMR (δ, CDCl₃): 2.08 (3H)s; 2.32 (6H)s; 2.64 (2H)m; 3.37 (3H)s; 3.78 (3H)s; 6.83 (2H)s; and 7.22 (2H)s.

EXAMPLE 10

The procedure of Example 9 is repeated, starting with the requisite reagents, to give the following compounds:
N-(11-acetyl-4″-deoxy-4″-oleandomycyl)-N′-(o-methoxybenzyl)urea; N-(11-acetyl-4″-deoxy-4″-oleandomycyl)-N′-(m-methoxybenzyl)urea; N-(11-propionyl-4″-deoxy-4″-oleandomycyl)-N′-(p-methoxybenzyl- )urea; and N-(11-propionyl-4"-deoxy-4"-oleandomycyl)-N'-(o-methoxybenzyl)urea.

EXAMPLE 11

N-(11-Acetyl-4"-deoxy-4"-oleandomycyl)-N'-(o-aminobenzyl)urea

To a well stirred and cooled (0° C) solution of 2.0 g. (2.7 mmoles) of 11-acetyl-4"-deoxy-4"-amino-oleandomycin and .65 ml. of pyridine in 50 ml. of dry methylene chloride is added rapidly 10 ml. of a 0.3M phosgene chloroform solution.

The reaction mixture is concentrated under reduced pressure, and the residual yellow foam dissolved in 50 ml. of dry methylene chloride. The solution is cooled in an ice bath and is then treated with 2.5 ml. of triethylamine followed immediately by 1.8 g. of o-aminobenzylamine dihydrochloride. After stirring in the cold for one hour, the reaction is quenched with water (75 ml.) and the pH of the aqueous wash adjusted to 9.5 with 1N aqueous sodium hydroxide solution. The organic phase is separated, dried over sodium sulfate and concentrated in vacuo to dryness to give 3.0 g. of the product as a yellow foam.

Further purification by chromatographing on a silica gel-acetone packed column gives 1.5 g. of pure product.

NMR (δ, CDCl₃): 2.06 (3H)s; 2.32 (6H)s; 2.65 (2H)m; 3.39 (3H)s; and 6.48–7.43 (4H)m.

EXAMPLE 12

The procedure of Example 11 is employed, starting with the appropriate reagents, to give the following compounds:

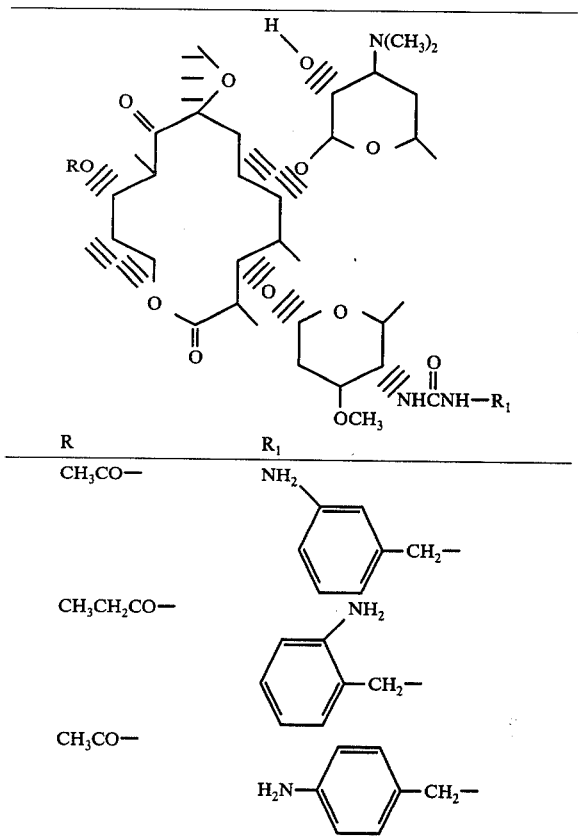

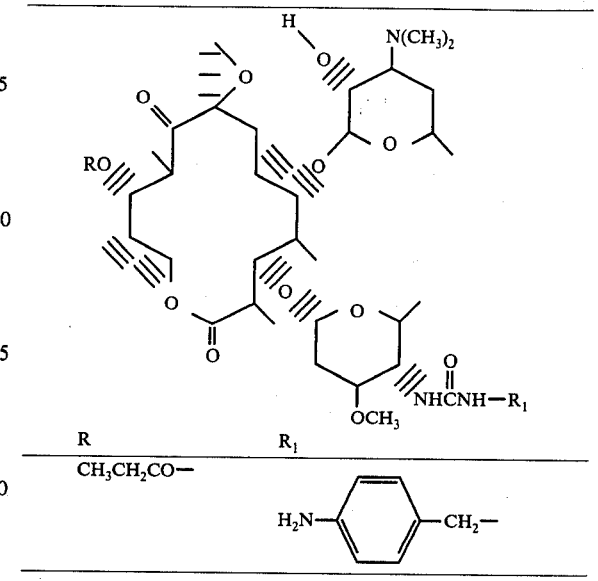

EXAMPLE 13

N-(11-Acetyl-4"-deoxy-4"-oleandomycyl)-N'-(4-pyridylmethyl)urea

To a well stirred and cooled (0° C.) solution of 2.0 g. (2.7 mmoles) of 11-acetyl-4"-deoxy-4"-amino-oleandomycin and .65 ml. of pyridine in 50 ml. of dry methylene chloride is added rapidly 7.24 ml. of a .41M chloroform solution of phosgene.

The reaction mixture is concentrated in vacuo to a foam, which is dissolved in 50 ml. of methylene chloride. The solution is subsequently cooled to ice bath temperatures and treated with .93 ml. of 4-aminomethylpyridine. After one hour of stirring in the cold the reaction mixture is treated with 100 ml. of methylene chloride and 75 ml. of water. The water is separated and fresh water mixed with the methylene chloride. The pH of the aqueous layer is adjusted to 9.5 with 6N aqueous sodium hydroxide solution. The organic phase is separated, dried over sodium sulfate and concentrated to dryness to give 2.3 g. of the product as a yellow foam.

Further purification is effected by chromatographing on a silica gel column using 20% methanol-80% acetone (v:v) as the eluate. In this manner 1.5 g. of pure product is isolated.

NMR (δ, CDCl₃): 2.07 (3H)s; 2.33 (6H)s; 2.70 (2H)m; 3.43 (3H)s; 7.29 (2H)s; and 8.54 (2H)s.

In a similar manner is prepared N-(11-acetyl-4"-deoxy-4"-oleandomycyl)-N'-(2-pyridylmethyl)urea.

NMR (δ, CDCl₃): 2.03 (3H)s; 2.31 (6H)s; 2.67 (2H)m; 3.39 (3H)s; 8.5–8.69 (1H)m and 7.05–7.91 (3H)m.

EXAMPLE 14

N-(11-Acetyl-4"-deoxy-4"-oleandomycyl)-N'-(2-furylmethyl)urea

In a manner similar to the procedure of Example 13, 2.0 g. (2.7 mmoles) of 11-acetyl-4"-deoxy-4"-amino-oleandomycin is converted to 11-acetyl-4"-deoxy-4"-isocyanato-oleandomycin, which on treatment with 870 mg. of furylmethylamine gives, after chromatographing on silica gel, 1.59 g. of product.

NMR (δ, CDCl₃): 2.07 (3H)s; 2.31 (6H)s; 2.67 (2H)m; 3.40 (3H)s; 6.11–6.36 and 7.19–7.41 (3H)m.

In like manner is prepared N-(11-propionyl-4"-deoxy-4"-oleandomycyl)-N'-(2-furylmethyl)urea and N-(11-acetyl-4"-deoxy-4"-oleandomycyl)-N'-(3-furylmethyl)urea.

EXAMPLE 15

The procedure of Example 13 is repeated, starting with the requisite reagents, to give the following compounds:

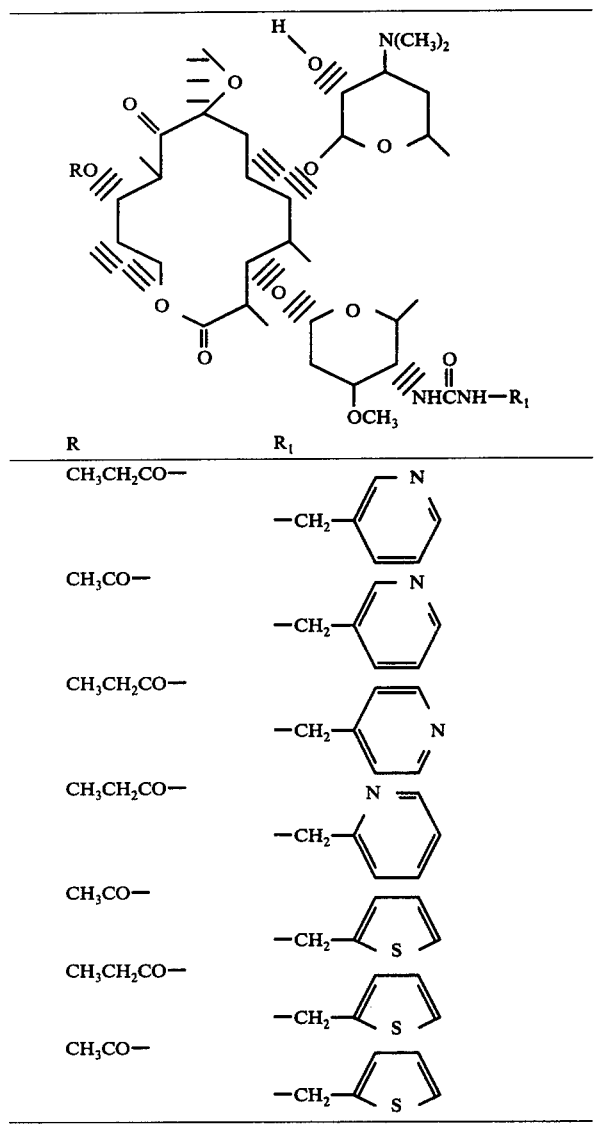

EXAMPLE 16

N-(11-Acetyl-4"-deoxy-4"-oleandomycyl)-N'-(3-hydroxy-2-pyridyl)urea

To 2.03 g. (2.7 mmoles) of 11-acetyl-4"-isocyanato-oleandomycin in 50 ml. of dry methylene chloride is added 600 mg. (5.4 mmoles) of 2-amino-3-hydroxypyridine, and the resulting solution allowed to stir for one hour. The reaction mixture is washed with water and the water layer discarded. Fresh water is layered over the organic phase and the pH adjusted to 7.5 with 6N-aqueous sodium hydroxide solution. The methylene chloride layer is separated, dried over sodium sulfate and concentrated under reduced pressure to give 3.6 g. of a white foam.

The sample is further purified by chromatographing over silica gel using acetone eluate. Combined fractions (5 ml. each) 115-770 are concentrated in vacuo to give 800 mg. of pure product.

NMR (δ, CDCl₃): 2.10 (3H)s; 2.31 (6H)s; 2.68 (2H)m; 3.47 (3H)s; 6.52-6.83 (1H)m; 7.28-7.5 (1H)m; and 7.84-8.01 (1H)m.

EXAMPLE 17

Starting with the appropriate reagents and employing the procedure of Example 16, the following compounds are synthesized:

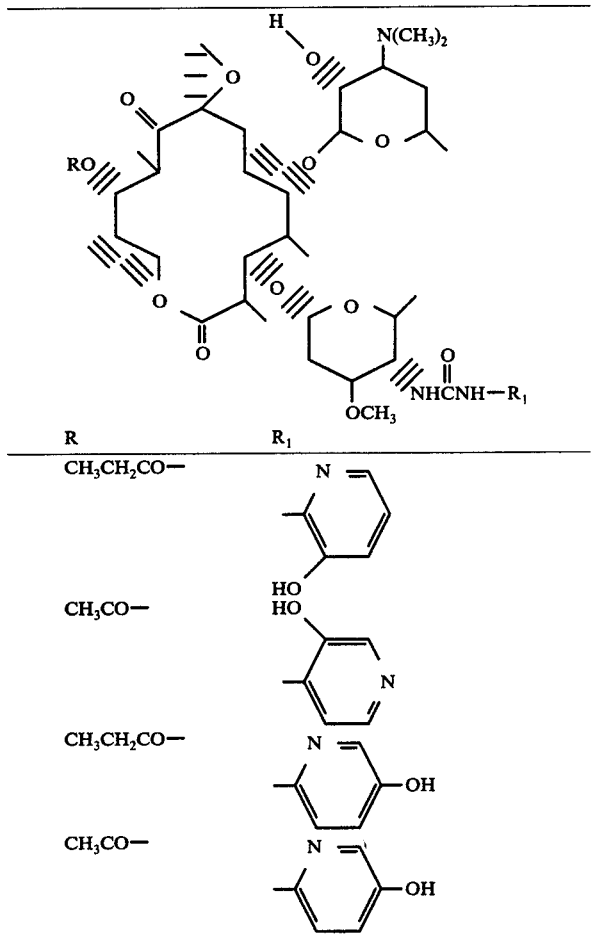

EXAMPLE 18

N-(11-Acetyl-4"-deoxy-4"-oleandomycyl)-N'-phenylurea

A reaction mixture comprising 25 g. (3.4 mmoles) of 11-acetyl-4"-deoxy-4"-amino-oleandomycin and .41 ml. (3.8 mmoles) of phenylisocyanate in 25 ml. of dry methylene chloride at 0° C. is allowed to stir for one hour and warm to room temperature. The reaction mixture is treated with 100 ml. of methylene chloride and 100 ml. of water. The pH of the water layer is adjusted to 9.9 with 1N aqueous sodium hydroxide and the methylene chloride layer separated, dried over sodium sulfate and concentrated in vacuo to dryness. The residual foam is chromatographed on silica gel, the fractions (5 ml.

each) being monitored for purity using thin layer chromatography (dimethylformamide/CH$_3$OH 1:3 via volume). Fractions 45–90 are combined and concentrated to give 226 mg. of a white foam.

NMR (δ, CDCl$_3$); 2.06 (3H)s; 2.31 (6H)s; 2.71 (2H)m; 3.43 (3H)s; and 7.25–7.56 (5H)m.

EXAMPLE 19

N-(11-Acetyl-4''-deoxy-4''-oleandomycyl)-N'-(p-chlorophenyl)urea

Three grams (4.1 mmoles) of 11-acetyl-4''-deoxy-4''-amino-oleandomycin in 50 ml. of dry methylene chloride under a nitrogen atmosphere and cooled to 0° C. is treated with 740 mg. (4.1 mmoles) of p-chlorophenylisocyanate. The reaction mixture is allowed to warm to room temperature and stirred at ambient temperatures for one hour. Methylene chloride (100 ml.) and water (100 ml.) are added to the reaction mixture and the pH of the water layer adjusted to 9.9 with 1N aqueous sodium hydroxide. The organic phase is separated, dried over sodium sulfate and concentrated in vacuo to a yellow foam.

The residual product is further purified by chromatographing on silica gel, the fraction, 5 ml. each, being monitored by thin layer chromatography (CHCl$_3$/CH$_3$OH/NH$_4$OH 9:1:0.1 via volume). Fractions 115–155 are combined and stripped under reduced pressure to give 716 mg. of the product as a white foam.

NMR (δ, CDCl$_3$): 2.07 (3H)s; 2.34 (6H)s; 2.69 (2H)m; 3.44 (3H)s; and 7.12 and 7.31 (4H).

EXAMPLE 20

Starting with the the reagents and employing the procedure of Example 19, the following congeners are prepared:

N-(11-acetyl-4''-deoxy-4''-oleandomycyl)-N'-(m-tolyl)urea

NMR (δ, CDCl$_3$): 2.08 (3H)s; 2.35 (6H)s; 2.70 (2H)m; 3.48 (3H)s; 6.78–7.38 (4H)m.

N-(11-acetyl-4''-deoxy-4''-oleandomycyl)-N'-(p-tolyl)urea

NMR (δ, CDCl$_3$): 2.07 (3H)s; 2.32 (6H) and (3H) broad s; 3.47 (3H)s; and 7.13 and 7.35 (4H).

N-(11-acetyl-4''-deoxy-4''-oleandomycyl)-N'-(o-chlorophenyl)urea

NMR (δ, CDCl$_3$): 2.10 (3H)s; 2.30 (6H)s; 2.70 (2H)m; 3.5 (3H)s; and 6.8–8.1 (4H)m.

N-(11-acetyl-4''-deoxy-4''-oleandomycyl)-N'-(p-methoxyphenyl)urea

NMR (δ, CDCl$_3$): 2.07 (3H)s; 2.35 (6H)s; 2.67 (2H)m; 3.47 (3H)s; 3.83 (3H)s; and 6.89 and 7.34 (4H).

EXAMPLE 21

The procedure the Example 19 is again repeated, starting with thre requisite reagents, to provide the following compounds:

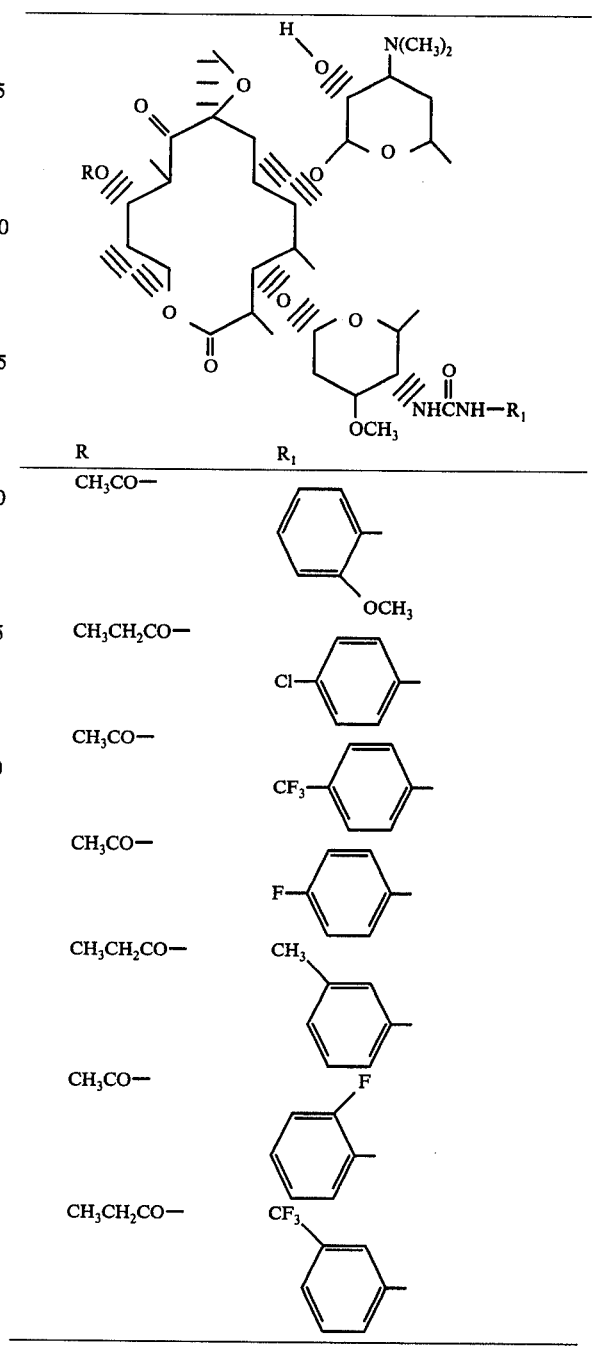

EXAMPLE 22

N-(11-Acetyl-4''-deoxy-4''-oleandomycyl)-N'-(p-methoxybenzoyl)urea

To a solution of 3.0 g. (4.1 mmoles) of 11-acetyl-4''-deoxy-4''-amino-oleandomycin in 50 ml. of dry methylene chloride at 25° C. is added 660 mg. (4.5 mmoles) of p-methoxybenzyl isocyanate. The mixture is allowed to stir at 25° C. for 0.5 hours, after which the solvent is removed under reduced pressure.

The residual yellow foam is chromatographed over silica gel using acetone as the eluate. The fractions, which are comprised of 5 ml. each, are monitored with thin layer chromatography. Those fractions containing the pure product are combined and concentrated to give 440 mg. of the product as a colorless amorphous solid.

NMR (δ, CDCl₃): 2.11 (3H)s; 2.32 (6H)s; 2.72 (2H)m; 3.47 (3H)s; 3.92 (3H)s; and 7.02 and 8.01 (4H).

In a similar manner is prepared:
N-(11-acetyl-4''-deoxy-4''-oleandomycyl)-N'-(m-methylbenzyl)urea NMR (δ, CDCl₃): 2.08 (3H)s; 2.32 (6H)s; 2.47 (3H)s; 2.71 (2H)m; 3.42 (3H)s; and 7.28–7.84 (4H)m.
and N-(11-acetyl-4''-deoxy-4''-oleandomycyl)-N'-(p-chlorobenzoyl)urea NMR (δ, CDCl₃): 2.05 (3H)s; 2.27 (6H)s; 2.65 (2H)m; 3.35 (3H)s; and 7.37 and 7.94 (4H).

EXAMPLE 23

Employing the procedure of Example 22, and starting with the appropriate reagents, the following compounds are synthesized: N-(11-acetyl-4''-deoxy-4''-oleandomycyl)-N'-(p-fluorobenzoly)urea; N-(11-acetyl-4''-deoxy-4''-oleandomycyl)-N'-(m-trifluoromethylbenzoyl)urea; N-(11-propionyl-4''-deoxy-4''-oleandomycyl)-N'-(o-chlorobenzoyl)urea; N-(11-propionyl-4''-deoxy-4''-oleandomycyl)-N'-(o-methylbenzoyl)urea; N-(11-propionyl-4''-deoxy-4''-oleandomycyl)-N'-(o-fluorobenzoyl)urea; N-(11-propionyl-4''-deoxy-4''-oleandomycyl)-N'-(m-trifluoromethylbenzoyl)urea;
and N-(11-acetyl-4''-deoxy-4''-oleandomycyl)-N'-(o-fluorobenzoyl)urea.

PREPARATION A

4''-Deoxy-4''-amino-oleandomycins

I. 11-Acetyl-4''-deoxy-4''-oxo-oleandomycin a. 11,2'-Diacetyl-4''-deoxy-4''-oxo-oleandomycin To a 4.5 g. of N-chlorosuccinimide, 50 ml. of benzene and 150 ml. of toluene in a dry flask fitted with a magnetic stirrer and nitrogen inlet and cooled to −5° C. is added 3.36 ml. of dimethylsulfide. After stirring at 0° C. for 20 min., the contents are cooled to −25° C. and treated with 5.0 g. of 11,2'-diacetyl-oleandomycin in 100 ml. of toluene. Cooling and stirring are continued for 2 hrs. followed by the addition of 4.73 ml. of triethylamine. The reaction mixture is allowed to stir at 0° C. for 15 min., and is subsequently poured into 500 ml. of water. The pH is adjusted to 9.5 with 1N aqueous sodium hydroxide and the organic layer separated, washed with water and a brine solution and dried over sodium sulfate. Removal of the solvent in vacuo gives 4.9 g. of the desired product as a foam.

NMR (δ, CDCl₃): 3.48 (3H)s; 2.61 (2H)m; 2.23 (6H)s and 2.03 (6H)s.

b. 11-Acetyl-4''-deoxy-4''-oxo-oleandomycin

A solution of 4.0 g. of 11,2'-diacetyl-4''-deoxy-4''-oxo-oleandomycin in 75 ml. of methanol is allowed to stir at room temperature overnight. The reaction mixture is concentrated under reduced pressure to give the product as a foam. A diethyl ether solution of the residue, on treatment with hexane, gives 2.6 g. of the product as a white solid, m.p. 112°–117° C.

NMR (δ, CDCl₃): 3.43 (3H)s; 2.60 (2H)m, 2.23 (6H)s and 2.01 (3H)s.

Similarly, by empolying 11,2'-dipropionyl-4''-deoxy-4''-oxo-oleandomycin or 11-propionyl-2'-acetyl-4''-deoxy-4''-oxo-oleandomycin in the above procedure, 11-propionyl-4''-deoxy-4''-oxo-oleandomycin is prepared.

II. 11-Acetyl-4''-deoxy-4''-amino-oleandomycin

To a suspension of 10 g. of 10% palladium-on-charcoal in 100 ml. of methanol is added 21.2 g. of ammonium acetate and the resulting slurry is treated with a solution of 20 g. of 11-acetyl-4''-deoxy-4''-oxo-oleandomycin in 100 ml. of the same solvent. The suspension is shaken at room temperature in a hydrogen atmosphere at an initial pressure of 50 p.s.i. After 1.5 hrs., the catalyst is filtered and the filtrate is added with stirring to a mixture of 1200 ml. of water and 500 ml. of chloroform. The pH is adjusted from 6.4 to 4.5 and the organic layer is separated. The aqueous layer, after a further extraction with 500 ml. of chloroform, is treated with 500 ml. of ethyl acetate and the pH adjusted to 9.5 with 1N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of the purified product, m.p. 157°–160° C.

NMR (δ, CDCl₃): 3.41 (3H)s; 2.70 (2H)m; 2.36 (6H)s and 2.10 (3H)s.

The other epimer, which exists in the crude foam to the extent of 20–25%, is obtained by gradual concentration and filtration of the mother liquors.

In a similar manner, starting with 11-propionyl-4''-deoxy-4''-oxo-oleandomycin in the above procedure, gives 11-propionyl-4''-deoxy-4''-amino-oleandomycin.

What is claimed is:

1. A compound selected from the group consisting of:

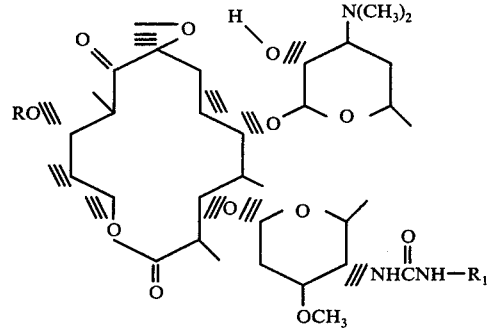

and a pharmaceutically acceptable acid addition salt thereof, wherein R is alkanoyl having from two to three carbon atoms; and R₁ is selected from the group consisting of hydrogen, pyridylmethyl, furylmethyl, thenyl, hydroxypyridyl, phenyl, benzyl and substituted phenyl and benzyl wherein said substituent is selected from the group consisting of methyl, chloro, fluoro, methoxy, amino and trifluoromethyl.

2. A compound of claim 1 wherein R is acetyl.

3. The compound of claim 2, N-(11-acetyl-4''-deoxy-4''-oleandomycyl)-N'-(p-methoxybenzyl)urea.

4. The compound of claim 2, N-(11-acetyl-4''-deoxy-4''-oleandomycyl)-N'-(p-chlorobenzyl)urea.

5. The compound of claim 2, N-(11-acetyl-4''-deoxy-4''-oleandomycyl)-N'-(o-chlorobenzyl)urea.

6. The compound of claim 2, N-(11-acetyl-4''-deoxy-4''-oleandomycyl)-N'-(m-methylbenzyl)urea.

7. The compound of claim 2, N-(11-acetyl-4''-deoxy-4''-oleandomycyl)-N'-(m-tolyl)urea.

8. The compound of claim 2, N-(11-acetyl-4''-deoxy-4''-oleandomycyl)-N'-(o-methylbenzyl)urea.

9. A compound selected from the group consisting of:

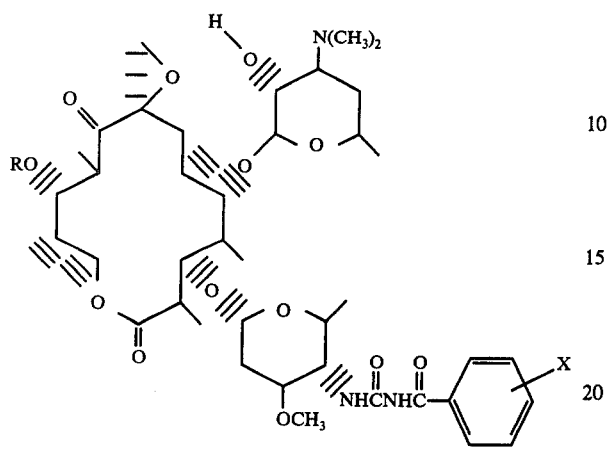

and a pharmaceutically acceptable salt thereof, wherein R is alkanoyl having two to three carbon atoms; and X is selected from group consisting of methyl, methoxy, fluoro, chloro and trifluoromethyl.

10. A compound of claim 9 wherein R is acetyl.

11. The compound of claim 10, N-(11-acetyl-4''-deoxy-4''-oleandomycyl)-N'-(m-methylbenzoyl)urea.

12. The compound of claim 10, N-(11-acetyl-4''-deoxy-4''-oleandomycyl)-N'-(p-methoxybenzoyl)urea.

13. A compound selected from the group consisting of

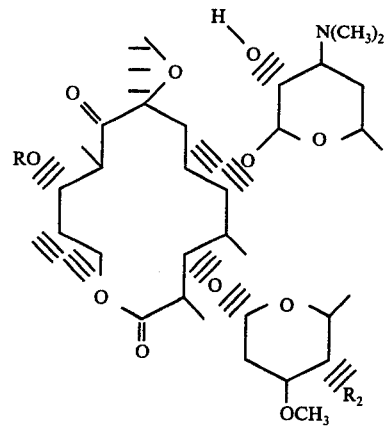

wherein R is alkanoyl having from two to three carbon atoms; $R_2$ is selected from the group consisting of —N=C=O and —NHCN; and the pharmaceutically acceptable acid addition salts wherein $R_2$ is —NHCN.

14. A compound of claim 13 wherein R is acetyl.

15. The compound of claim 14, 11-acetyl-4''-deoxy-4''-isocyanato-oleandomycin.

* * * * *